United States Patent [19]

Sih

[11] 4,252,747
[45] Feb. 24, 1981

[54] 2-DECARBOXY-2-HYDROXYMETHYL-19-HYDROXY-19-METHYL-6-OXO-PGF$_1$ COMPOUNDS

[75] Inventor: John C. Sih, Kalamazoo, Mich.

[73] Assignee: The Upjohn Company, Kalamazoo, Mich.

[21] Appl. No.: 126,496

[22] Filed: Mar. 3, 1980

Related U.S. Application Data

[62] Division of Ser. No. 54,720, Jul. 5, 1979.

[51] Int. Cl.$^3$ ............................................. C07C 177/00
[52] U.S. Cl. ..................................... 568/379; 568/380
[58] Field of Search ..................................... 260/586 R

[56] References Cited

U.S. PATENT DOCUMENTS 4,158,667  6/1979  Axen ..................................... 260/413

Primary Examiner—Robert Gerstl
Attorney, Agent, or Firm—Robert A. Armitage

[57] ABSTRACT

The present invention provides novel 2-decarboxy-2-hydroxymethyl-19-hydroxy-19-methyl-6-oxo-PGF$_1$ compounds which are useful for pharmacological purposes, e.g., anti-asthmatic indications.

9 Claims, No Drawings

2-DECARBOXY-2-HYDROXYMETHYL-19-HYDROXY-19-METHYL-6-OXO-PGF$_1$ COMPOUNDS

CROSS REFERENCE TO RELATED APPLICATION

The present invention is a divisional application of U.S. Ser. No. 054,720, filed July 5, 1979.

DESCRIPTION

1. BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-hydroxymethyl-19-hydroxy-19-methyl-6-oxo-PGF$_1$ compounds. The novel prostacyclin analogs are useful for pharmacological purposes, e.g., as anti-asthmatic agents. The preparation and use of these compounds is incorporated here by reference from U.S. Ser. No. 054,720, filed July 5, 1979.

2. PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides
a prostacyclin-type compound of the formula

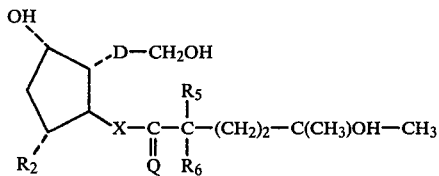

wherein D is —(CH$_2$)$_2$—CO—CH$_2$—L$_2$— or —CH$_2$—CO—CH$_2$—L$_3$—
wherein L$_2$ is
 (1) —(CH$_2$)$_j$—, wherein j is one to 4, inclusive,
 (2) —(CH$_2$)$_q$—CF$_2$—, wherein q is one, 2, or 3, or
 (3) —CH=CH—,
wherein L$_3$ is
 (1) —(CH$_2$)$_n$—, wherein n is one to 5, inclusive,
 (2) —(CH$_2$)$_p$—CF$_2$—, wherein p is 2, 3, or 4, or
 (3) —CH$_2$—CH=CH—;
wherein Q is oxo, α-H:β-H, α-OH:β-R$_4$, or α-R$_4$:β-OH,
wherein R$_4$ is hydrogen or alkyl of one to 4 carbon atoms, inclusive,
wherein R$_2$ is hydrogen, hydroxyl, or hydroxymethyl;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein X is
 (1) trans—CH=CH—,
 (2) cis—CH=CH—,
 (3) —C≡C—, or
 (4) —CH$_2$CH$_2$—.

DESCRIPTION OF THE PREFERRED EMBODIMENTS

The present invention particularly relates to the following compounds:
2-Decarboxy-2-hydroxymethyl-5-oxo-19-hydroxy-19-methyl-PGF$_1$,
2-Decarboxy-2-hydroxymethyl-5-oxo-16,16-difluoro-19-hydroxy-19-methyl-PGF$_1$,
2-Decarboxy-2-hydroxymethyl-6-oxo-19-hydroxy-19-methyl-PGF$_1$, and
2-Decarboxy-2-hydroxymethyl-6-oxo-16,16-difluoro-19-hydroxy-19-methyl-PGF$_1$.

I claim:

1. A prostacyclin-type compound of the formula

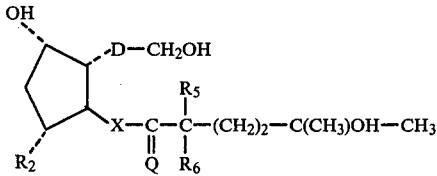

wherein D is —(CH$_2$)$_2$—CO—CH$_2$—L$_2$— or —CH$_2$—CO—CH$_2$—L$_3$—
wherein L$_2$ is
 (1) —(CH$_2$)$_j$—, wherein j is one to 4, inclusive,
 (2) —(CH$_2$)$_q$—CF$_2$—, wherein q is one, 2, or 3, or
 (3) —CH=CH—,
wherein L$_3$ is
 (1) —(CH$_2$)$_n$—, wherein n is one to 5, inclusive,
 (2) —(CH$_2$)$_p$—CF$_2$—, wherein p is 2, 3, or 4, or
 (3) —CH$_2$—CH=CH—;
wherein Q is oxo, α-H:β-H, α-OH:β-R$_4$, or α-R$_4$:β-OH,
wherein R$_4$ is hydrogen or alkyl of one to 4 carbon atoms, inclusive,
wherein R$_2$ is hydrogen, hydroxyl, or hydroxymethyl;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein X is
 (1) trans-CH=CH—,
 (2) cis-CH=CH—,
 (3) —C≡C—, or
 (4) —CH$_2$CH$_2$—.

2. A compound according to claim 1, wherein D is —(CH$_2$)$_2$—CO—CH$_2$—L$_2$—, wherein L$_2$ is —(CH$_2$)$_j$, wherein j is one to 4, inclusive.

3. A compound according to claim 2, wherein D is —(CH$_2$)$_2$—CO—CH$_2$—(CH$_2$)$_2$—, Q is α-OH:β-H, R$_2$ is hydroxyl, and X is trans-CH=CH—.

4. 2-Decarboxy-2-hydroxymethyl-5-oxo-19-hydroxy-19-methyl-PGF$_1$, a compound according to claim 3.

5. 2-Decarboxy-2-hydroxymethyl-5-oxo-16,16-difluoro-19-hydroxy-19-methyl-PGF$_1$, a compound according to claim 3.

6. A compound according to claim 1, wherein D is —CH$_2$—CO—CH$_2$—L$_3$, wherein L$_3$ is —(CH$_2$)$_n$—, wherein n is one to 5, inclusive.

7. A compound according to claim 6, wherein D is —CH$_2$—CO—CH$_2$—(CH$_2$)$_3$—, Q is α-OH:β-H, R$_2$ is hydroxyl, and X is trans-CH=CH—.

8. 2-Decarboxy-2-hydroxymethyl-6-oxo-19-hydroxy-19-methyl-PGF$_1$, a compound according to claim 7.

9. 2-Decarboxy-2-hydroxymethyl-6-oxo-16,16-difluoro-19-hydroxy-19-methyl-PGF$_1$, a compound according to claim 7.

* * * * *

UNITED STATES PATENT OFFICE
CERTIFICATE OF CORRECTION

Patent No. 4,252,747　　　　　　　　　Dated 24 February 1981

Inventor(s) John C. Sih

It is certified that error appears in the above-identified patent and that said Letters Patent are hereby corrected as shown below:

The Related U.S. Application Data should read

-- Division of Ser. No. 54,720, Jul. 5, 1979, U.S. Patent 4,225,507. --

Column 1, line 10, "U.S. Ser. No. 054,720, filed July 5, 1979." should read -- U.S. Ser. No. 054,720, filed July 5, 1979, now United States Patent 4,225,507. --; lines 23-24, "U.S. Ser. No. 054,720, filed July 5, 1979" should read -- U.S. Patent 4,225,507 --.

Signed and Sealed this

Twenty-sixth Day of May 1981

[SEAL]

*Attest:*

RENE D. TEGTMEYER

*Attesting Officer*　　　*Acting Commissioner of Patents and Trademarks*